(12) United States Patent
Chana

(10) Patent No.: US 9,259,330 B2
(45) Date of Patent: Feb. 16, 2016

(54) SURGICAL POSITIONING APPARATUS

(75) Inventor: Gursharan Singh Chana, Birmingham (GB)

(73) Assignee: Gursharan Singh Chana, Birmingham, West Midlands (GB)

( * ) Notice: Subject to any disclaimer, the term of this patent is extended or adjusted under 35 U.S.C. 154(b) by 618 days.

(21) Appl. No.: 13/577,056

(22) PCT Filed: Feb. 2, 2011

(86) PCT No.: PCT/GB2011/050173
§ 371 (c)(1),
(2), (4) Date: Nov. 28, 2012

(87) PCT Pub. No.: WO2011/095804
PCT Pub. Date: Aug. 11, 2011

(65) Prior Publication Data
US 2013/0066322 A1    Mar. 14, 2013

Related U.S. Application Data

(60) Provisional application No. 61/301,563, filed on Feb. 4, 2010.

(30) Foreign Application Priority Data

Feb. 4, 2010    (GB) .................................. 1001838.0

(51) Int. Cl.
| A61F 2/46 | (2006.01) |
| A61B 5/107 | (2006.01) |
| A61B 5/00 | (2006.01) |
| A61B 19/00 | (2006.01) |
| A61F 2/32 | (2006.01) |
| A61F 2/30 | (2006.01) |

(52) U.S. Cl.
CPC .................. *A61F 2/4657* (2013.01); *A61F 2/46* (2013.01); *A61F 2/4609* (2013.01); *A61B 5/1072* (2013.01); *A61B 5/4528* (2013.01); *A61B 2019/461* (2013.01); *A61F 2/32* (2013.01); *A61F 2002/30617* (2013.01); *A61F 2002/4658* (2013.01); *A61F 2002/4687* (2013.01); *A61F 2250/0097* (2013.01)

(58) Field of Classification Search
CPC . A61F 2/4657; A61F 2002/4658; A61F 2/46; A61F 2/4609
See application file for complete search history.

(56) References Cited

U.S. PATENT DOCUMENTS

| 5,122,145 A | 6/1992 | Fishbane |
| 5,700,268 A | 12/1997 | Bertin |

(Continued)

FOREIGN PATENT DOCUMENTS

WO        WO 01/30247        5/2001

*Primary Examiner* — Nicholas Woodall
(74) *Attorney, Agent, or Firm* — Alston & Bird LLP

(57) ABSTRACT

A surgical positioning apparatus (400) comprises a surgical positioning device (412) and a levelling device (422). The surgical positioning device (412) comprises a securing assembly (416), a locating arrangement (418) securable to the securing assembly in a selected position of the locating arrangement, and an indicating arrangement (420) securable to the securing assembly in a selected position of the Indicating arrangement. The locating arrangement (418) comprises a locating member (432) to locate the positioning device in a desired orientation relative to a first article. The indicating arrangement (420) comprises an indicating member (488) to indicate the position of a second article relative to the first article. The levelling device (422) can be mounted on the surgical positioning device (412) to facilitate orientation of the surgical positioning device relative to the vertical.

25 Claims, 17 Drawing Sheets

(56) References Cited

U.S. PATENT DOCUMENTS

| | | | |
|---|---|---|---|
| 6,027,507 A * | 2/2000 | Anderson et al. | 606/102 |
| 6,193,724 B1 * | 2/2001 | Chan | 606/102 |
| 2003/0093080 A1 * | 5/2003 | Brown et al. | 606/102 |
| 2009/0076519 A1 | 3/2009 | Iversen | |

* cited by examiner

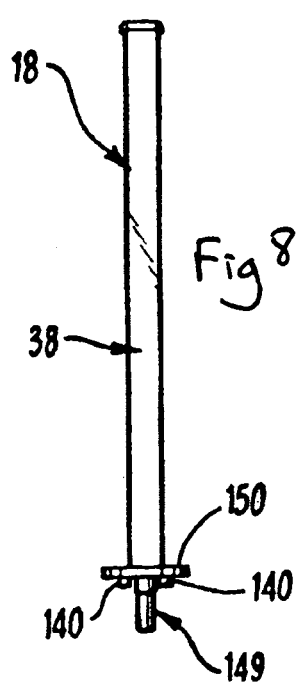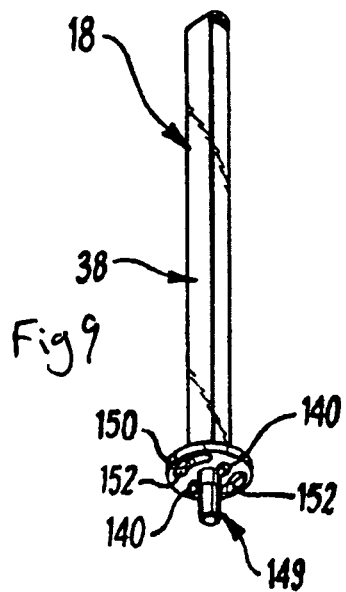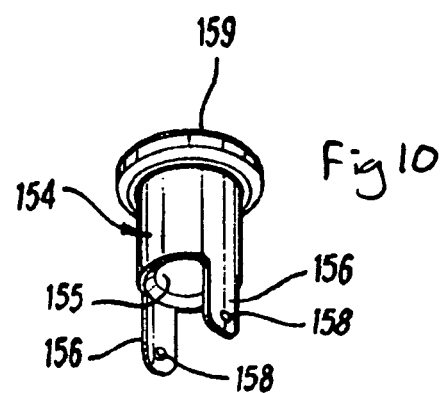

SURGICAL POSITIONING APPARATUS

CROSS-REFERENCE TO RELATED APPLICATIONS

This application is the U.S. National Stage filed under 35 U.S.C. 371 of International Application No. PCT/GB2011/050173 filed Feb. 2, 2011, which designates the U.S. and was published by the International Bureau in English on Aug. 11, 2011, and which claims the benefit of U.S. Provisional Application No. 61/301,563, filed Feb. 4, 2010 and GB Patent Application No. 1001838.0, filed on Feb. 4, 2010, all of which are hereby incorporated by reference in their entirety.

This invention relates to levelling devices. More particularly, but not exclusively, this invention relates to levelling devices for use with surgical apparatus. This invention may also relate to apparatus, such as surgical apparatus, incorporating leveling devices. Embodiments of the invention relate to surgical positioning devices and apparatus for use in determining the length and position of a leg during hip replacement surgery.

During hip replacement surgery, it is important to ensure that the patient has leg length equality and accurate lateralisation of the hip joint. This is particularly the case during minimal invasive surgery. Present devices used for this purpose do not provide the necessary precision.

According to one aspect of this invention, there is provided a surgical positioning apparatus comprising a surgical positioning device and a levelling device, the surgical positioning device comprising a securing assembly, a locating arrangement securable to the securing assembly in a selected position of the locating arrangement, an Indicating arrangement securable to the securing assembly in a selected position of the indicating arrangement, wherein the locating arrangement comprises a locating member to locate the positioning device in a desired orientation relative to a first article, and the indicating arrangement comprises an indicating member to indicate the position of a second article relative to the first article, and wherein the levelling device can be mounted on the surgical positioning device to facilitate orientation of the surgical positioning device relative to the vertical.

According to another aspect of this invention, there is provided a surgical positioning apparatus comprising a surgical positioning device as described above and a marker element which can be mounted on the first article, the marker element comprising a co-operating formation to co-operate with the locating member and hold the locating member on the marker element.

The levelling device may comprise a levelling member, a carrier for carrying the levelling member, a support upon which the carrier is mounted, and an attaching arrangement to attach the carrier to the support in a desired position relative thereto, wherein the levelling member is suspended from the carrier for pendulous motion relative thereto The levelling member may comprise a liquid filled member having a transparent wall. A bubble of a gas, such as air may be provided in the liquid filled member. The transparent wall may have a marked region to indicate when the levelling device is at a desired position, such as horizontal. Thus, when the bubble is aligned with the marked region, the levelling device is at the aforesaid desired position. The leveling device may be a spirit level, and may be cylindrical. The levelling device may include a holder for the liquid filed member. The holder may correspond in size and shape to the liquid filled member to receive the liquid filled member.

According to another aspect of this invention, there is provided a levelling device comprising a levelling member, a carrier for carrying the levelling member, a support upon which the carrier is mounted, and a attaching arrangement to secure the carrier to the support in a desired position relative thereto, wherein the leveling member is suspended from the carrier for pendulous motion relative thereto The levelling member may comprise an elongate portion extending from the carrier. The levelling member may further include an enlarged portion on the elongate portion. The enlarged portion may be provided to provide weight to the levelling member, allowing the levelling member to be suspended substantially vertically from the carrier. The levelling member may include an Indicator portion at a lower end thereof. The leveling device may further include an Indicator formation associated with the Indicator portion. The carrier may be positioned such that when the carrier is arranged substantially vertically, the Indicator portion is aligned with the indicator formation.

The attaching arrangement may comprise a positioning member and a securing member co-operable with the positioning member to secure the positioning member in a desired position. The positioning member may be provided on the carrier. The securing member may be provided on the support. The securing member may be adjustable.

The positioning member may comprise a ball member. The securing member may comprise an engagement member for engaging the ball member. The ball member may be mounted on the carrier. The engagement member may be on the support.

The securing member may be movable towards the positioning member to secure the positioning member. The securing member may be movable away from the positioning member to release the positioning member and allow movement of the carrier relative to the support. The securing member may comprise a threaded portion adapted to co-operate with a threaded element on the support. The threaded element may be rotatable to move the adjustable member linearly between the securing angular lease positions.

The carrier may comprise a generally C shaped member having an upper region and a lower region. The levelling member may be suspended from the upper region of the carrier. A pivot arrangement may be provided at the upper region of the carrier to suspend the leveling member therefrom. The pivot arrangement may allow three dimensional pendulous motion of the levelling member. The Indicator portion may be provided on the carrier. The Indicator portion may be provided at the lower region of the carrier.

The levelling device may include a mounting arrangement to mount the leveling device on a surgical apparatus. The mounting arrangement may comprise a fastening member on the support. The fastening member may comprise a main portion and an outwardly extending flange on the main portion. The main portion may comprise an Insertion portion insertable into the surgical apparatus.

The mounting arrangement may further include a reaction member moveably mounted on the fastening member. The reaction member may extend around the rotating member, and may comprise a sleeve mounted on the locating member. A lip may extend outwardly from the sleeve. Urging means may extend around the sleeve, and may extend between the flange and the lip.

A finger may be provided on the reaction member. The flange may define an aperture to receive therethrough the finger, which may extend downwardly from the reaction member. In one embodiment, the mounting arrangement comprises two fingers arranged centrally opposite each other on the reaction member. The flange may define a respective aperture for the, or each, finger, which may be a curved slot.

The, or each, finger may be received through the respective aperture in the flange, and the, or each, finger may have an Inwardly extending detent formation thereon to co-operate with a respective fastening formation on a mounting member on the surgical apparatus.

Alliteratively, the levelling member may comprise a liquid filled member having a transparent wall. A bubble of a gas, such as air may be provided in the liquid filed member. The transparent wall may have a marked region to indicate when the levelling device is at a desired position, such as horizontal. Thus, when the bubble is aligned with the marked region, the levelling device is at the aforesaid desired position. The levelling device may be a spirit level, and may be cylindrical. The levelling device may include a holder for the liquid filled member. The holder may correspond in size and shape to the liquid filled member to receive the liquid filed member.

The locating arrangement may be movable relative to the securing assembly. The locating arrangement may be linearly movable relative to the securing assembly. The locating arrangement may be slidable relative to the securing assembly. The locating arrangement may comprise an elongate member, which may have a main axis. The locating arrangement may be rotatably movable relative to the main axis. The locating member may be elongate.

The locating arrangement may comprise an elongate main portion, which may be substantially generally oblong in configuration. The locating member may be provided at one end of the elongate main portion. Thus, in one embodiment, the position of the securing assembly can be adjusted relative to the locating arrangement angularly and linearly. The locating member may comprise at least one projection. The locating member may comprise a V-shaped projection. The locating arrangement may comprise two V-shaped projections arranged opposite each other. The, or each, V-shaped projection may comprise a pin.

The locating arrangement may further include a guide projection to guide the locating member on the marker element. The guide projection may extend downwardly from the main portion, and may be substantially cylindrical. The locating arrangement may further include a fastening assembly to fasten the locating arrangement to the marker element.

In another embodiment, the locating arrangement may comprise an elongate member, which may be in the form of an elongate post. The elongate member may have an H-shaped cross-sectional profile.

A fastening assembly may be provided on the elongate member. The fastening assembly may comprise a clamping arrangement, which may comprise first and second clamping members movable between clamping and released conditions. The first clamping member may be pivotally attached to the second clamping member at a main pivot. A fastening link may be pivotally attached to the first clamping member, desirably at a first pivot member. The first pivot member may be opposite the main pivot.

The fastening link may be pivotally attached to a proximal pivot member, which may be mounted on a lever. The lever may have a distal pivot member, which may be provided adjacent the proximal pivot member. The distal pivot member may pivotally attach the lever to a second pivot member. The second pivot member may be provided on the second clamping member opposite the main pivot.

The lever may be pivotally movable between a clamping position in which the first and second clamping members are pulled against one another, and a released position, in which the clamping members are moved apart from one another. The fastening assembly may include a location means, which the clamping arrangement can clamp when the first and second clamping members are in the clamping position. The location means may comprise a location body and a clampable member.

The clamping arrangement may clamp the clampable member. The clampable member may comprise a ball member. The location body may be configured to mount the locating arrangement on the marker element. The location body may comprise a marker engaging portion and may also include an upper mounting portion. The clampable member may be provided on the upper mounting portion.

The location means may include a locking member, and the marker engaging portion may define a pathway therethrough into which the locking member can be received. The locking member may define an aperture, which may have a narrower section and a wider section. The locking member may be slidable within the pathway between locking and non-locking positions. When the locking member is in the locking position, a portion of the marker element may be received in the smaller section, thereby locking the marker element to the fastening assembly.

The marker element may have a head having a wider securing portion and a narrower neck portion. When the locking member is in the locking position, the smaller section of the aperture may be around the neck portion. In one embodiment, the smaller section of the aperture is narrower than the securing portion, thereby securing the marker element to the location body.

In the embodiment mentioned in the immediately preceding paragraph, when the locking member is in the non-locking position, the larger section of the aperture may be disposed around the neck portion. In that embodiment, the larger section of the aperture may be wider than the securing portion, thereby allowing the securing portion to pass therethrough.

The locking member may have front and rear flange members preventing inadvertent removal of the locking from the pathway.

The Indicating arrangement may be movable relative to the surgical positioning device. The Indicating arrangement may be movable linearly relative to the surgical positioning device, and may be slidable relative to the surgical positioning device.

The surgical positioning device may include an extension member, which may be elongate, and may comprise an elongate arm. The extension member may extend from the locating arrangement to the Indicating arrangement, and may define a slot for co-operating with the securing assembly.

The Indicating arrangement may be provided at one end region of the extension member. The Indicating arrangement may comprise an indicating member, which may extend transverse to the extension member. In one embodiment, the Indicating member may extend substantially orthogonally to the extension member. The indicating member may include an Indicating portion that extends transverse to the extension member, and conveniently extends substantially orthogonally to the extension member.

In one embodiment, the indicating member is fixed to the extension member. In another embodiment, the indicating member is adjustably movable relative to the extension member. In this embodiment, the indicating member may be removable from the extension member.

The indicating arrangement may comprise a locking arrangement on the extension member. The locking arrangement may comprise a fixed member mounted on the extension member. The fixed member may be configured to receive the Indicating member.

The fixed member may have a co-operating member to cooperate with the Indicating member. The co-operating member may comprise a co-operating collar.

Desirably, the indicating member defines locking formations to co-operate with the co-operating member. The locking formation may be first and second indentations defined in the indicating member.

In one embodiment, a fastening lever may be pivotally mounted on the extension member, desirably at an end region thereof. The fastening lever may have a cam member thereon which can engage the Indicating member. The fastening lever may be movable from a non-fastening position to a fastening position to fasten the indicating member to the surgical positioning device.

In one embodiment, when the fastening lever is moved from the non-fastening position to the fastening position, the cam member may push the indicating member against a region of the extension member, thereby fastening the Indicating member to the extension member.

The locking arrangement may include a locking member mounted on the fixed member to lock the indicating member thereto. Desirably, the locking member is threaded to cooperate with threads on the fixed member. The fixed member may have an externally threaded end portion and the locking member may be correspondingly internally threaded.

One embodiment of the apparatus is suitable for use in hip replacement surgery, wherein the first article may comprise a patient's pelvis, and the second article may comprise the patient's femur. In one use of this embodiment, the marker element may be mounted on the lilac crest of the patient's pelvis, and the Indicating member may indicate a positioning mark on the patient's femur, which may be on the greater trochanter of the patient's femur.

The marker element may comprise an insertion element, which may comprise a datum screw. The marker element may have a shank having a screw thread, which may be a self tapping screw thread. The marker element may have a head, which may have a co-operating formation which may be a recess to receive the locating member. The recess may have planar sides to prevent rotation of the locating member relative to the marker element. The co-operating formation may be configured to co-operate with a drive element, such as a key to drive the marker element into the first article.

In one embodiment, the recess may have the profile of a regular polygon, such as a hexagon, and the locating member may have an outer profile of a regular polygon to correspond with the polygonal profile of the recess. Thus, the locating member can be inserted into the recess in the head of the marker element in one of a plurality of different orientations, depending upon the number of faces of the polygonal profile of the recess and the locating member.

In another embodiment, the marker element comprises a locating formation to locate the locating member thereon. The locating formation may be a locating recess, which may be a V-shaped recess. Desirably, the marker element has two locating recesses, both of which may be V-shaped recesses. The two locating recesses may be defined in the head of the marker element, and may be arranged opposite each other.

The marker element may define a drive recess to receive a drive element. The drive recess may have a profile of a regular polygon, such as a hexagon. The locating recesses may be defined in the head of the marker element on opposite sides of the drive recess. In this embodiment, the locating arrangement may comprise two locating members, and each of which may have a V-shaped configuration, corresponding to the shape of the corresponding locating recesses.

The marker element may define a central guide recess to receive the locating projection. The central guide recess may be defined between the locating recesses, and may extend into the marker element from the drive recess. Desirably, the guide recess extends axially into the marker element. The central guide recess may be substantially cylindrical.

The marker element may have a fastening formation to fasten the locating arrangement to the marker element. The fastening formation may be a recess in the marker element. The recess may be a J-shaped recess. The marker element may comprise two fastening formations opposite each other. Each of the fastening formations may be a J-shaped recess.

The securing assembly may further include a holding member and securing means for securing the locating arrangement to the holding member. In one embodiment, the securing means may comprise first and second securing members for securing the locating arrangement to the holding member.

The first and second securing members may comprise first and second screws. The holding member may define first and second threaded apertures to receive the first and second screws respectively. The first screw may engage the locating arrangement when the first screw is received in the first aperture to secure the locating arrangement to the securing assembly.

The holding member may define a main receiving hole for receiving the locating arrangement therethrough. The main receiving hole may overlap with the first aperture whereby the threaded portion of the first securing member can engage the locating arrangement when the locating arrangement is received in the main receiving hole, and the first securing member is received in the first aperture. The main receiving hole and the first aperture may be transverse to each other, and are conveniently substantially mutually orthogonal.

The securing assembly may also comprise a guide member to guide movement of the indicating arrangement relative to the holding member. The guide member may be mounted on the holding member, and may comprise an outwardly extending guide portion and a connecting portion to connect the guide portion to the holding member.

The guide member may be received by the indicating arrangement. Where the securing assembly comprises an extension member having a slot, the guide member may be received through the slot. When the guide member is received through the slot, the guide portion may extend across the slot and the connecting portion may extend through the slot.

The second aperture may be arranged such that the second securing member extends through the slot when the second securing member is received in the second aperture. The head of the second securing member may engage the extension member to secure the extension member to the securing assembly. In one embodiment, the main receiving hole and the second aperture may extend substantially parallel to each other.

In one embodiment, the securing assembly may comprise a first holding member mountable on the extension member. The first holding member may be a lower holding member and may be mountable beneath the extension member. The extension member may have an elongate formation extending along a major proportion of the length of the extension member. The elongate formation may cooperate with the securing assembly. The elongate formation may be a slot defined in the extension member. The securing assembly may include a second holding member, which may be mountable on the extension member. The second holding member may be mountable on top of the extension member.

At least one of the first and second holding members may have a projecting connection member which cooperates with the formation when the first or second holding member is mounted on the extension member. The, or each, projecting connection member may project through the slot to engage the other of the first and second holding members. The projecting connection members may include a first detent formation on one of the first and second holding members to cooperate with second formations on the other of the first and second holding members portion to secure the first and second holding members to each other and, thereby, to the extension member.

A securing lever may be pivotally mounted on one of the projecting connection members. The securing lever may include a cam member. An engaging member, which may be in the form of a flap member, may be pivotally mounted on the other of the first and second holding members. The cam member may urge the engaging member into engagement with the extension member when the securing lever is moved to a securing position, thereby securing the securing assembly and hence the locating arrangement in a desired position on the extension member.

One of the first and second holding members may define a passage for a locking slide. The locking slide may be slidably movable within the passage. The locking slide may define an aperture, which may be a rectangular aperture. The locating member may extend through the aperture. The first and second holding members may define apertures being of a corresponding shape to the cross-sectional profile of the elongate locating member, thereby to receive the elongate locating member therethrough.

When the locking slide is arranged within the passage, the elongate locating member may be movable longitudinally within the apertures defined by the first and second holding members. When the locking slide is slid within the passage to a locking position, the locking slide may engage the elongate locating member, thereby securing the elongate locating member in a desired position.

The elongate locating member may include a plurality of securing formations arranged therealong. The securing formations may comprise serrations. The locking slide may comprise a securing projection projecting into the aperture defined therein. The securing projection may engage the securing formations, when the locking slide is disposed in the locking position.

The surgical positioning apparatus may comprise a drive arrangement to drive the marker element into the first article. The drive arrangement may comprise a drive fitment, which may be mountable on a power tool. The drive fitment may comprise a drive member to be received in the drive recess of the marker element. The drive arrangement may further comprise a fastening assembly to fasten the drive arrangement to the marker element. The fastening assembly may comprise a bayonet type fixing.

The fastening assembly may comprise a projecting member on the main portion. The projecting member may extend outwardly from the main portion, and may comprise an outwardly extending flange. The fastening assembly may further include a reaction member movably mounted on the locating arrangement or the drive arrangement. The reaction member may extend around the locating arrangement or the drive arrangement and may comprise a sleeve slidably mounted on the locating arrangement or the drive arrangement. The reaction member may be provided on the elongate main portion.

The fastening assembly may comprise urging means extending from the projecting member to the reaction member to urge the reaction member away from the projecting member. The reaction member may comprise an outwardly extending lip. The urging means may extend between the lip and the projecting member. Where the reaction member comprises a sleeve, the outwardly extending lip may extend around the sleeve.

A finger may be provided on the reaction member. The projecting member may define an aperture to receive therethrough the finger, which may extend downwardly from the reaction member. Conveniently, the fastening assembly may comprise two fingers which may be arranged substantially opposite each other on the reaction member.

The projecting member may define two apertures, and the, or each, aperture may be a curved slot. The, or each, finger may be received through the, or a respective, aperture in the projecting member. The, or each, finger may have an inwardly extending detent formation thereon to cooperate with a respective fastening formation on the marker element.

Embodiments of the invention will now be described by way of example only, with reference to the accompanying drawings, in which:

FIG. 8 is a side view of a part of a locating arrangement used in surgical positioning apparatus;

FIG. 9 is a perspective view of the part of the locating arrangement shown in FIG. 8;

FIG. 10 is a perspective view of a part of a fastening assembly for use in the part of the locating arrangement shown in FIGS. 8 and 9;

Figure 1:
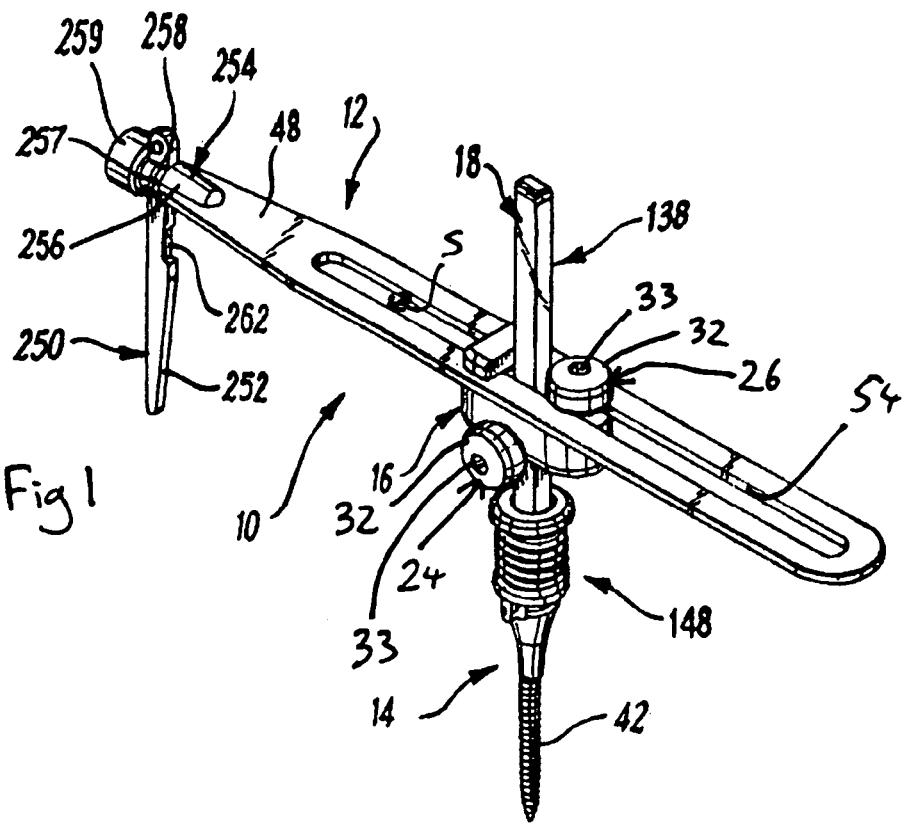
FIG. 1 is a perspective view of a surgical positioning apparatus.
Figure 2:
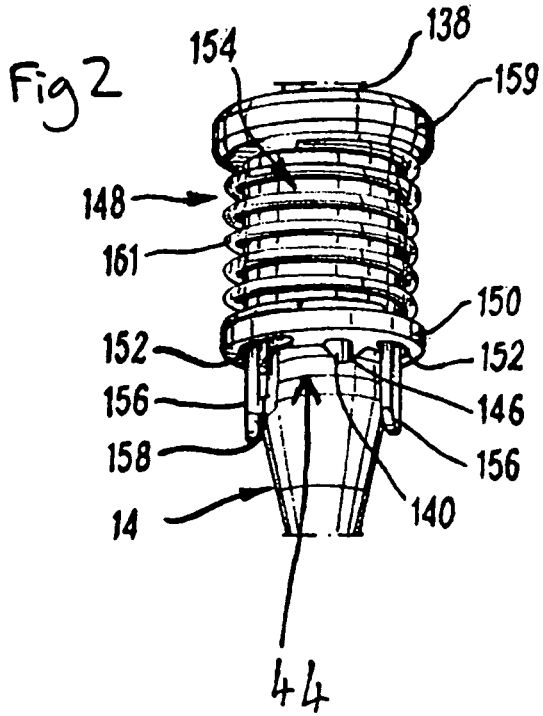
FIG. 2 shows a region of a marking element having a fastening assembly thereon.
Figure 3:
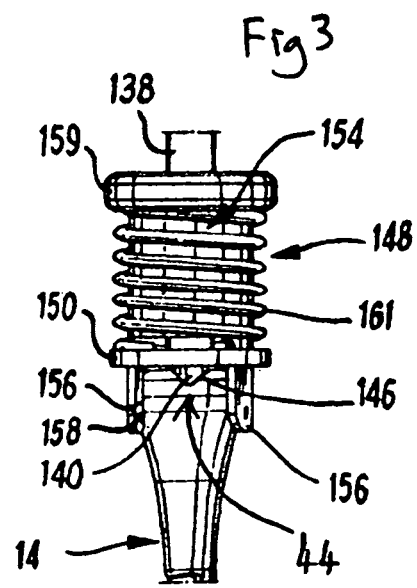
FIG. 3 is a side view of the marking element shown in FIG. 2.
Figure 4:
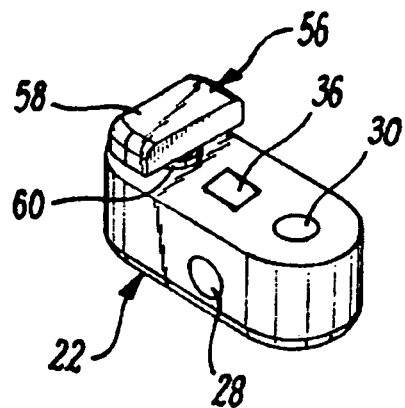
FIG. 4 is a perspective view of a holding member of a securing assembly.
Figure 5:
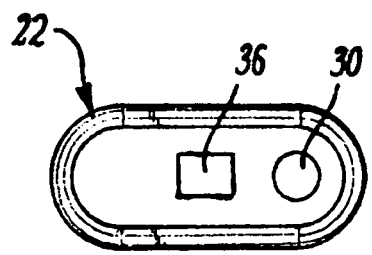
FIG. 5 is a bottom plan view of the holding member shown in FIG. 4.
Figure 6:
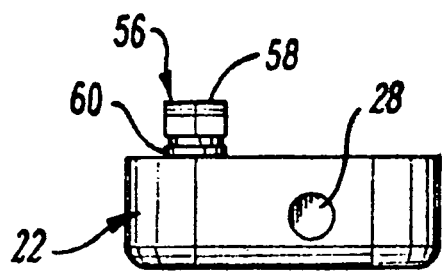
FIG. 6 is a side view of the holding member shown in FIG. 4.
Figure 7:
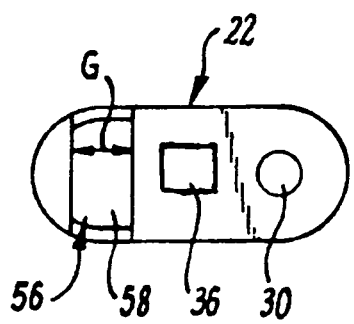
FIG. 7 is a top plan view of the holding member shown in FIG. 4.

FIG. 1 shows a surgical positioning apparatus 10, which comprises a surgical positioning device 12 and a marker element, in the form of a datum screw 14. The surgical positioning device 12 comprises a securing assembly 16, a locating arrangement 18, and an indicating arrangement 250. The securing assembly 16 comprises a holding member 22, and securing means comprising first and second securing members in the form of first and second securing screws 24, 26.

The holding member 22 defines first and second threaded screw receiving apertures 28, 30, shown in FIGS. 4 to 7. Each of the first and second securing screws 24, 26 has a head 32 and a threaded shank, as would be understood by those skilled in the art. The holding member also defines a rectangular main hole 36 to receive the locating arrangement, as explained below.

Each of the heads 32 defines a recess 33 having a hexagonal profile to receive a hexagonally profiled key, such as an Allen key, which can be used to ensure that the first and second securing screws 24, 26 are screwed in to the respective first and second threaded screw receiving apertures 28, 30 sufficiently tightly for the purposes of the use of the surgical positioning apparatus 10.

The locating arrangement 18 extends through the main hole 36 through the holding member 22 of the securing assembly 16.

Figure 11:
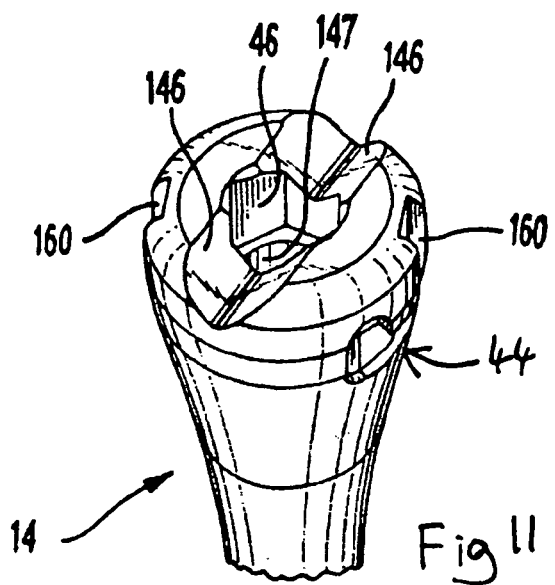
FIG. 11 is a perspective view of a top region of a marking element.
Figure 12:
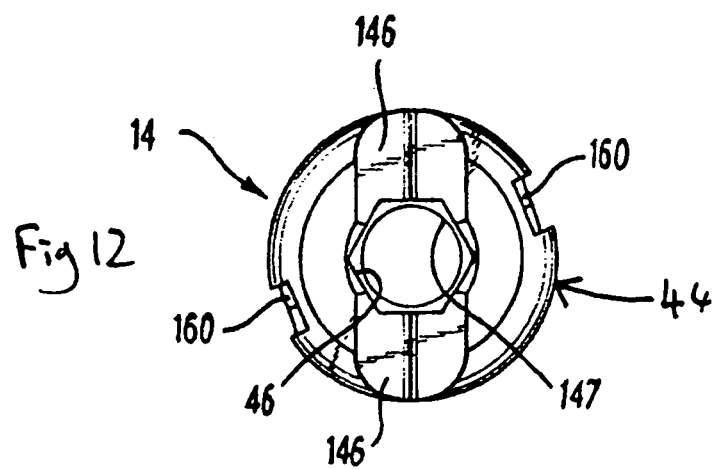
FIG. 12 is a top view of the marking element shown in FIG. 11.

The datum screw 14 comprises a threaded shank 42 and a head 44. The top of the head 44 (see FIGS. 11 and 12) defines a key receiving recess 46 having a profile of a regular hexagon. The key receiving recess 46 can receive a key, such as an Allen key, to drive the datum screw 14 into the iliac crest of a patients pelvis during total hip arthroplasty.

The datum screw 14 further defines two V-shaped locating recesses 146 on opposite sides of the hexagonal key receiving recess 46. A substantially cylindrical central guide recess 147 extends from the hexagonal key receiving recess 46 axially into the datum screw 14.

The locating arrangement 18 comprises a locating post 38 having a generally rectangular cross-sectional profile. Referring to FIGS. 8 and 9, the locating arrangement 18 further includes a pair of pins 140 of a corresponding shape to the V-shaped locating recesses 146, so that the pins 140 are a tight fit in the locating recesses 146. The locating arrangement further includes a substantially cylindrical guide projection 149 (see FIGS. 10 and 11), which can be received in the central guide recess 147.

The guide projection 149 is received in the central guide recess 147 to guide the locating arrangement onto the datum screw 14. The pins 140 are received in the V-shaped recesses 146 to arrange the locating arrangement 18 in the desired orientation.

The locating arrangement 18 further includes a fastening assembly 148 (see FIGS. 2, 3 and 8 to 10) to fasten the locating arrangement to the datum screw 14.

Figure 14:
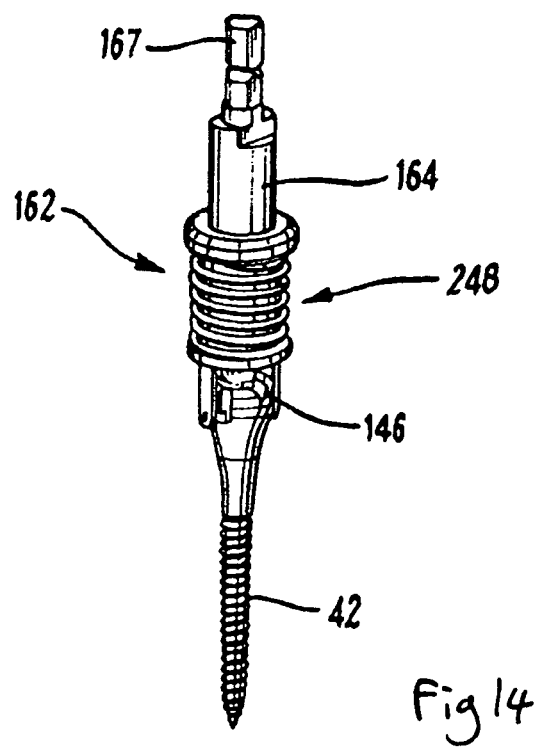
FIG. 14 is a perspective view of a marking element with a fastening assembly thereon.
Figure 15:
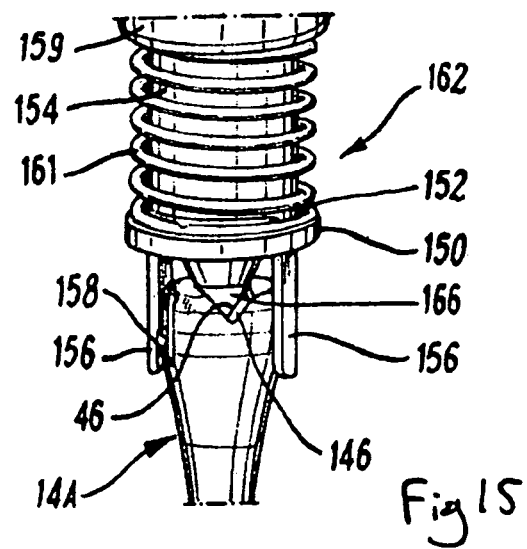
FIG. 15 is a close-up view of the marking element with the fastening assembly thereon.
Figure 16:
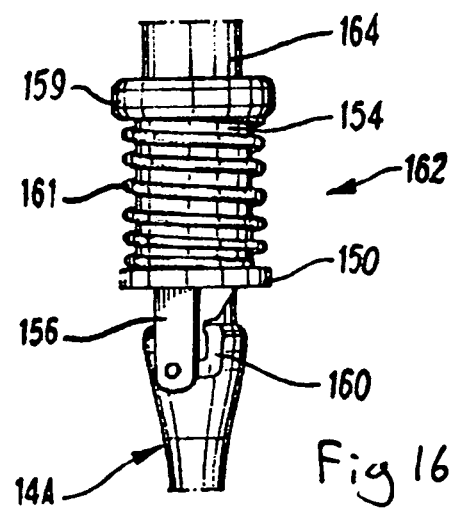
FIG. 16 is a side view of the marking element with the fastening assembly thereon.

In order to drive the datum screw 14 into the iliac crest of the patient, a drive arrangement 162 is provided (see FIGS. 14 to 16), which comprises a drive fitment 164 to be connected to a power tool, and a further fastening assembly 248, which is generally the same as the first mentioned fastening assembly 148, and operates in the same way. The fastening assemblies 148 and 248 are described in detail below.

The drive fitment 164 includes a drive member 166 having a hexagonally shaped profile, which is received in the hexagonal key receiving recess 46 to drive the datum screw 14. The drive fitment 164 also includes a mounting member 167 to mount the drive fitment on a power tool (not shown) to drive the datum screw 14 into the bone.

Referring back to FIGS. 1 and 4 to 7, when the locating arrangement 18 is received in the main hole 36 of the holding member 22, it can be secured therein by the first securing screw 24. The threaded aperture 28 overlaps the main hole 36 so that the shank of the first securing screw 24 engages the elongate generally rectangular post 38, thereby securing the locating arrangement 18 to the holding member 22 of the securing assembly 16.

It will be appreciated that the holding member 22 can be slid up and down the elongate generally rectangular post 38. When the desired position of the holding member 22 has been selected, the first securing screw 24 can be screwed into the threaded aperture 28 to engage the elongate generally rectangular post 38 to secure the locating arrangement 18 to the holding member 22.

Figure 17:
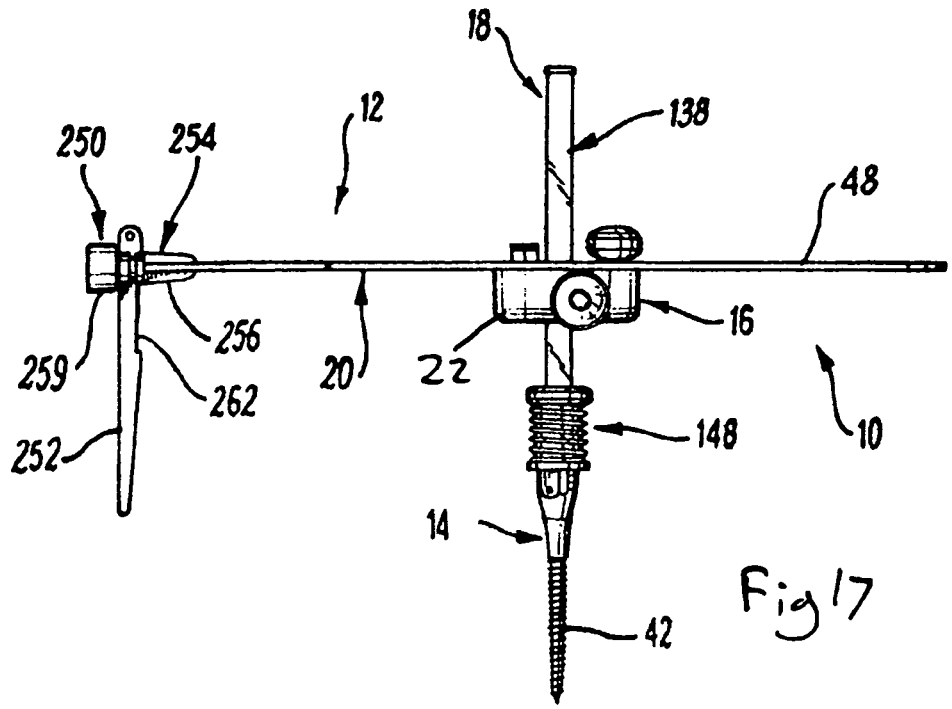
FIG. 17 is a side view of the positioning apparatus with a positioning member in a first position.
Figure 18:
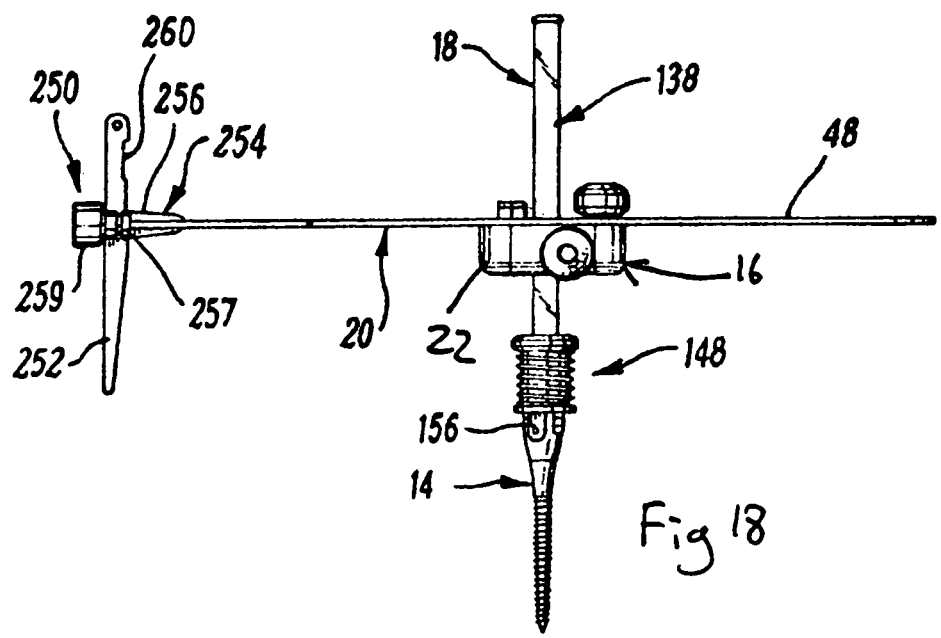
FIG. 18 is a side view of the positioning apparatus with the positioning member in a second position.

Referring to FIGS. 1, 17 and 18, the surgical positioning device 12 further includes an extension member in the form of an elongate arm 48. An adjustable indicating arrangement 250 is mounted at one end region of the elongate arm 48. The indicating arrangement comprises a movable indicating member 252, which is movable relative to the elongate arm 48 between a first position shown in FIG. 17 and a second position shown in FIG. 18. This allows the surgical positioning device 12 to accommodate differing anatomies of different patients.

The securing assembly 16 further includes a locking arrangement 254 to lock the Indicating member 252 in its first or second positions. The locking arrangement 254 comprises a fixed member 256 mounted on the elongate arm 48. The fixed member 256 defines an aperture 258 through which the indicating member 252 can be received. The fixed member 256 also has a co-operating collar 257 to cooperate with locking formations on the indicating member 252, as explained below.

The fixed member 256 has an externally threaded end portion on which an Internally threaded locking member 259 can be screwed. The locking member 259 may comprise a nut.

The indicating member 252 defines locking formations in the form of first and second indentations 260, 262 defined in the indicating member 252. The first and second indentations 260, 262 help secure the indicating member 252 in the first or second position.

The elongate arm 48 defines a positioning slot 54 which extends along a major proportion of the length of the elongate arm 48.

A guide member 56 is provided on the holding member 22. The guide member 56 comprises an outwardly extending guide portion 58 and a connecting portion 60 to connect the guide portion 58 to the holding member 22. In use, the holding member 22 and the guide member 56 are arranged such that the guide portion 58 is arranged to extend across an upper surface of the elongate arm 48, with the holding member 22 arranged beneath the elongate arm 48. The connecting portion 60 extends from the guide portion 58 to the holding member 22 through the positioning slot 54.

The guide portion 58 has a width G, which is less than the width S of the positioning slot 54 in the elongate arm 48. Thus, the guide portion 58 can be inserted through the positioning slot 54 and then twisted to its position shown in FIG. 2.

During total hip replacement surgery the placement of the femoral and acetabular implant will change the medial/lateral and proximal/distal position of the joint centre of rotation which may affect leg length and offset.

During surgery, as described above, the positioning apparatus 10 is arranged on the datum screw 14 in the patient's lilac crest, and the various components are fixed in the appropriate positions relative to the positions of the patient's bones. When the components of the positioning apparatus 10 have been so fixed, the positioning apparatus 10 is removed, and placed to one side for use after the surgery is finished.

After completion of the surgery, it is necessary to arrange the positioning apparatus back on the datum screw 14 in the patient's iliac crest. However, it is likely that the patient will have moved during surgery, and it is important that the positioning apparatus 10 and the patient are in the same position as they were before surgery. To this end, a levelling device 310 as described below is used.

Figure 19:
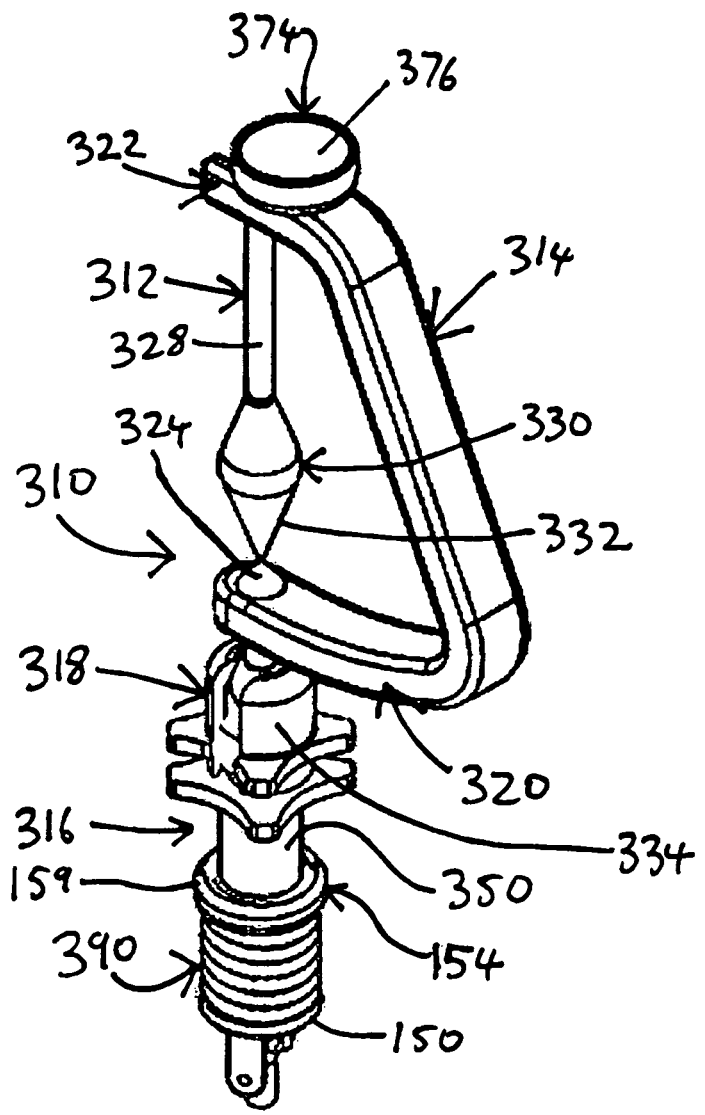
FIG. 19 is a perspective view of a levelling device.
Figure 20:
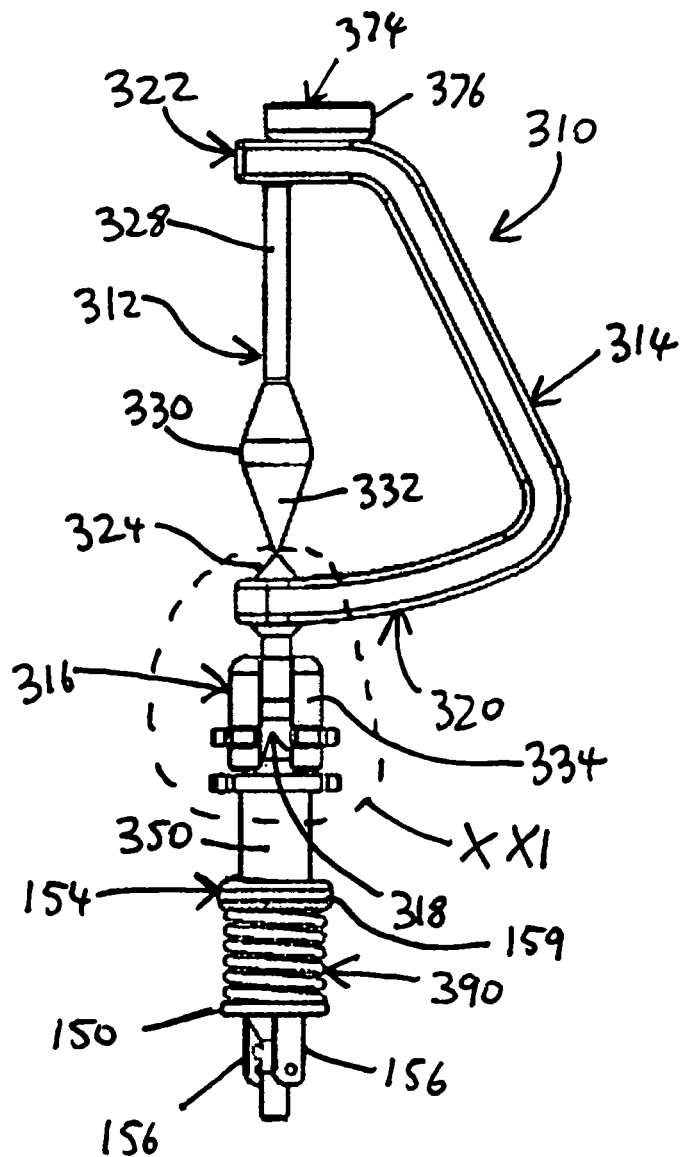
FIG. 20 is a side view of the leveling device shown in FIG. 1.
Figure 22:
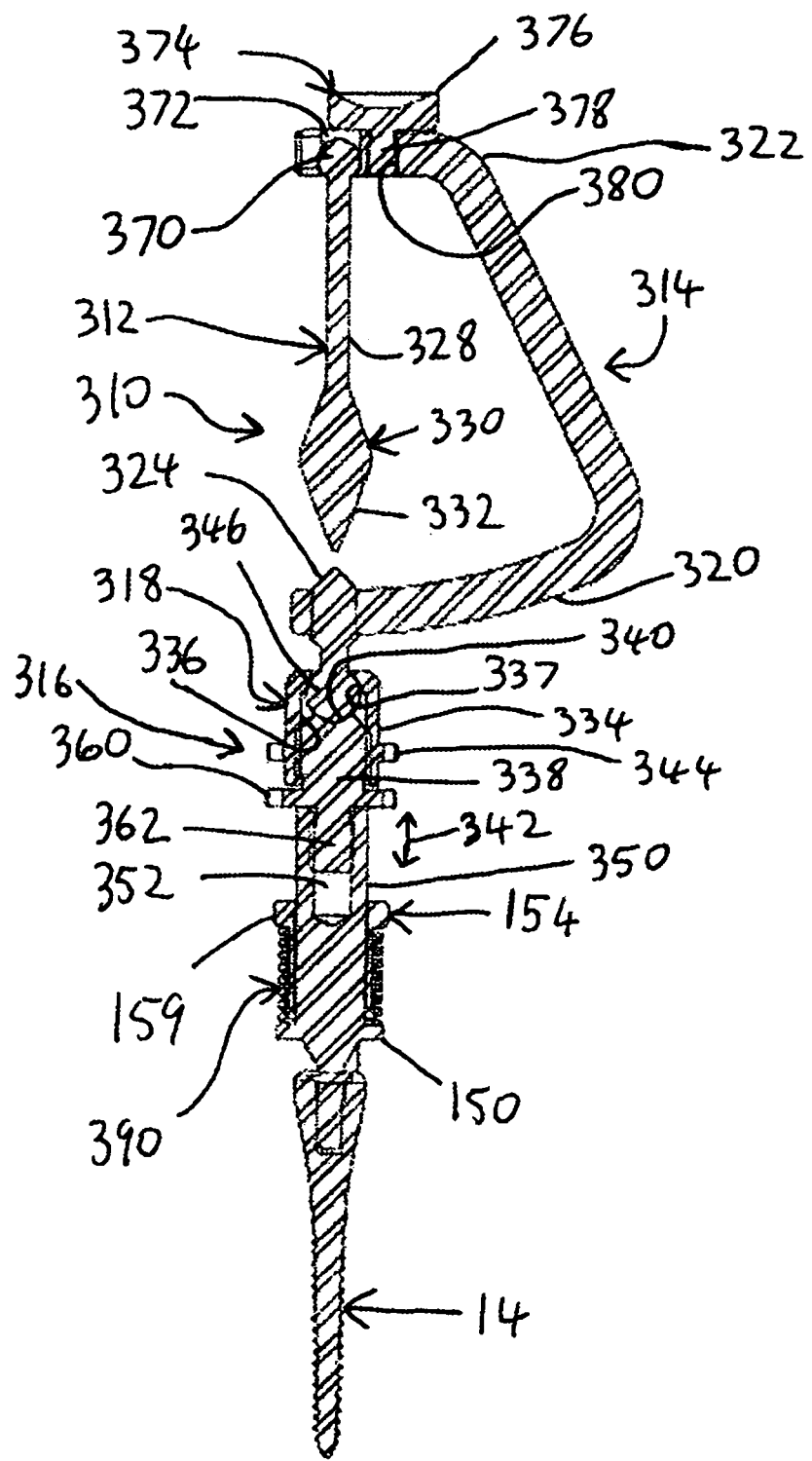
FIG. 22 is a sectional side view of the positioning apparatus shown in FIG. 19.

The levelling device 310 is shown in FIGS. 19, 20 and 22, and comprises a leveling member 312, a carrier 314 for carrying the levelling member 312, and a support 316 for supporting the carrier 314. The levelling device 310 further includes a securing arrangement 318 which secures the carrier 314 to the support 316. The carrier 314 is of a generally C shaped configuration, having a lower region 320 and an upper region 322. The levelling member 312 is suspended from the upper region 322 in a manner that allows three dimensional pendulous motion of the levelling member 312 relative to the carrier 314. The lower region 320 of the carrier 314 includes an indicator portion 324, in the form of a cone shaped member, the purpose of which is explained below.

The levelling member 312 comprises an elongate rod 328 pivotally mounted at the upper region 322 of the carrier 314, and a weight 330 at the lower end of the elongate member 328. The elongate rod 328 has a ball member 370 at its upper end, which is received in a recess 372 in the upper region of the carrier 314. The ball member is held in the recess by a holding member 374, comprising a wider disc shaped member 376, and a depending threaded member 378 which is threadably received in a threaded aperture 380 adjacent the recess 372. The disc shaped member 376 extends over the recess 372, thereby preventing inadvertent removal or dislodging of the ball member 370 in the recess 372.

The weight 330 comprises an Indicator portion in the form of an inverted conical member 332. The inverted conical member 332 is provided to indicate that the carrier 314 is vertical when the inverted conical member 332 is aligned with the indicator portion 324.

Figure 21:
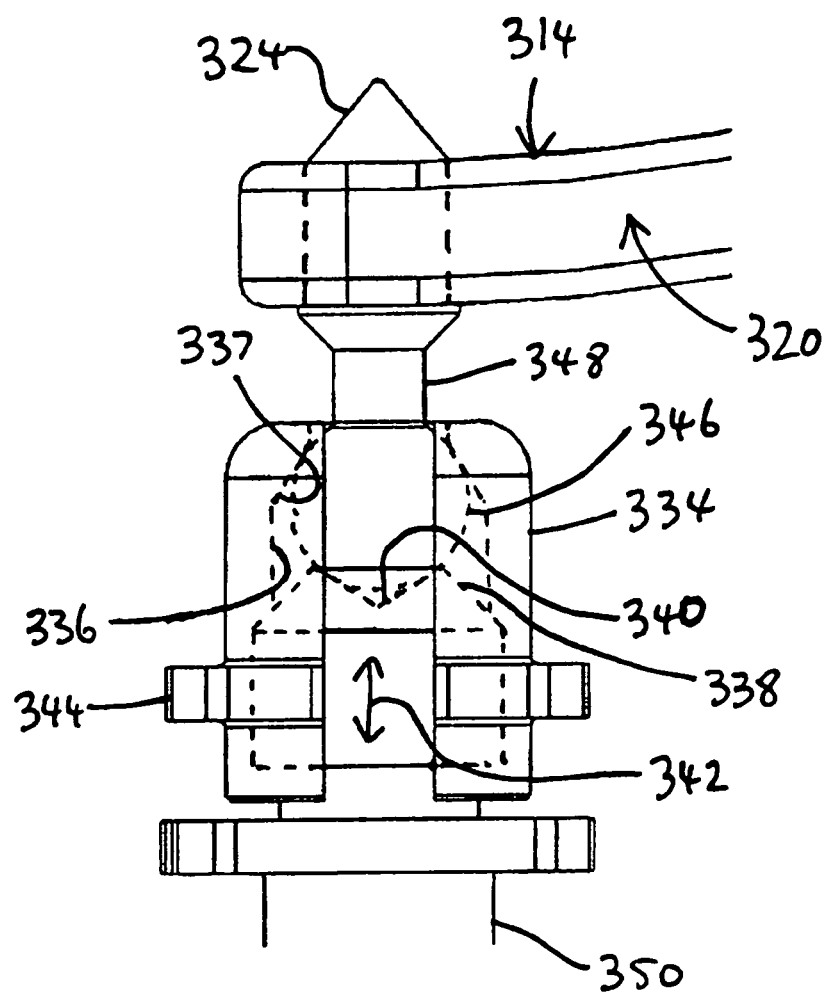
FIG. 21 is a close up view of the region marked XXI in FIG. 20.

The support 316 comprises a hollow body 334, which defines an Inner chamber 336 having tapering upper walls 337. The inner chamber 336 is represented by broken lines in FIG. 21.

The securing arrangement comprises a securing member 338 defining a recess 340. The securing member 338 is received in the chamber 336 of the body 334. The recess 340 has a V shaped profile.

The securing member 338 is moveable up and down, in the direction as shown by the double headed arrow 342 by rotation of a first turning member 344. The first turning member 344 is fixedly mounted on the hollow body 334. The hollow body 334 and the securing member 338 are correspondingly threaded so that the rotation of the turning member 344 in a direction into or out of the paper causes the hollow body 334 to rotate, which in turn moves the securing member 338 in one of the directions shown by the arrow 342, depending upon which way the first turning member 344 is turned.

A positioning member 346, in the form of a ball member is mounted on the lower region 320 of the carrier 314 by a substantially cylindrical shank 348.

The positioning member 346 is received within the chamber 336 and can be received by the recess 340 in the securing member 338. The securing member 338 can be moved upwardly by turning the turning member 344. This movement of the securing member 338 causes the securing member 338 to engage the positioning member 346 and push the positioning member 346 against the tapering wall 337 of the chamber 336. Thus, the positioning member 346 is secured against the tapering upper walls 337 within the chamber 336 in a desired position.

The positioning member 346 can be released by turning the turning member 344 in the opposite direction to move the securing member 338 downwardly, thereby disengaging the securing member 338 from the positioning member 346. This allows the position of the carrier 314 to be adjusted to a further position. The carrier 314 can then be secured in the further position by turning the turning member 344 so that the securing member 338 again engages the spherical member 346 to secure the spherical member 346 between the securing member 338 and the tapering wall 337.

The support 316 further includes a downwardly extending connecting portion 350 defining an internally threaded chamber 352. A second turning member 360 is fixedly mounted on the securing member 338, which also has a threaded depending member 362 thereon. The depending member 362 extends into the chamber 352, and threadably engages the internal threads therein. Turning of the second turning member 360 moves the securing member 338 in either direction indicated by the double headed arrow 342 relative to the connecting portion 350.

The connecting portion 350 has a fastening assembly 390 mounted thereon. The fastening assembly 390 connects the levelling device 310 to a further article, for example a surgical apparatus, or a marker, which can be inserted into a patient's bone. The fastening assembly 390 is the same as the fastening assemblies 148 and 248, and are described below. Where the description below describes a feature with reference to only one of the fastening assemblies, it will be appreciated that the other fastening assemblies also have that feature.

Each of the fastening assemblies 148, 248 and 390 comprise a flange 150 defining two curved slots 152 opposite each other. The flange 150 is fixedly mounted on the locating post 38 and extends radially outwardly therefrom. In the case of the further fastening assembly 248, the flange 150 is fixedly mounted on the drive fitment 164. In the case of the fastening assembly 390, the flange 150 is fixedly mounted on the connecting portion 350.

The fastening assembly 148 further includes a sleeve member 154 (see FIG. 12) which defines a hole 155 therethrough to slidably mount the sleeve member 154 around the locating post 38, and a pair of fingers 156 extend from the sleeve member 154. Each finger 156 extends through a respective one of the curved slots 152. A detent formation 158 is provided on, and extends inwardly from, each finger 156. The sleeve member 154 has a radially outwardly extending lip 159 extending therefrom. Urging means in the form of a spring 161 is arranged between the lip 159 and the flange 150.

Figure 13:
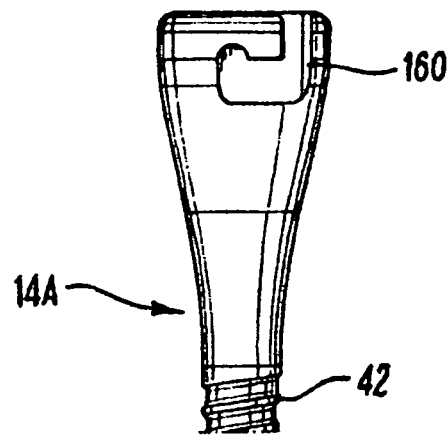
FIG. 13 is a side view of the upper region of the marking element shown in FIG. 11.

Referring to FIG. 13, the upper region of the datum screw 14 defines co-operating recesses 160, arranged opposite each other. The co-operating recesses 160 are generally J-shaped, and are configured to cooperate with the detent formations 158 in the manner of a bayonet type fitting, to fasten the locating arrangement 18, the drive arrangement 162 or the leveling device 310, to the datum screw 14. The spring 161 urges the lip 159 away from the flange 150, and thus assists in fastening the datum screw 14 to the locating arrangement 18, the drive arrangement, or the levelling device 310.

The above described embodiment of the surgical positioning apparatus 10 incorporating the levelling device 310 provides an initial datum measurement of the joint positioning prior to cutting the bone, and allows corrections to be made to alter the datum position according to estimates made from the x-rays prior to surgery. Then the patient's physiology can be adjusted using the trials/implants to meet the positioning shown by the surgical positioning apparatus 10.

Figure 23:
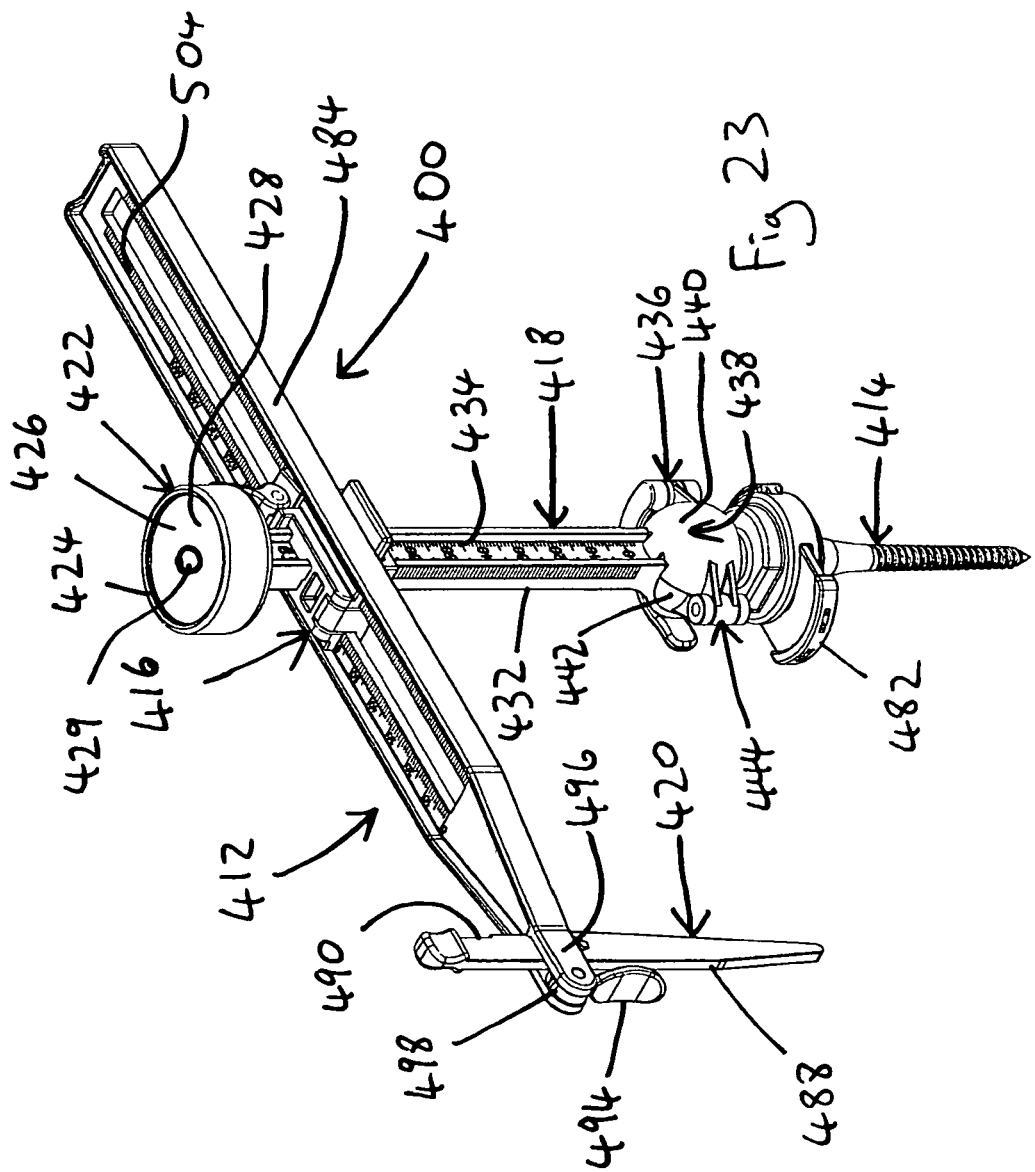
FIG. 23 is a perspective view of another embodiment of a surgical positioning apparatus.

A further embodiment of a surgical positioning apparatus is shown in FIGS. 23 to 30. The surgical positioning apparatus shown in FIG. 23 is generally designated 400.

The surgical positioning apparatus 400 comprises a surgical positioning device 412 and a marker element, in the form of a datum screw 414. The surgical positioning device 412 comprises a securing assembly 416, a locating arrangement 418, and an adjustable indicating arrangement 420. A levelling device 422 is provided on the locating arrangement 418.

Figure 24:
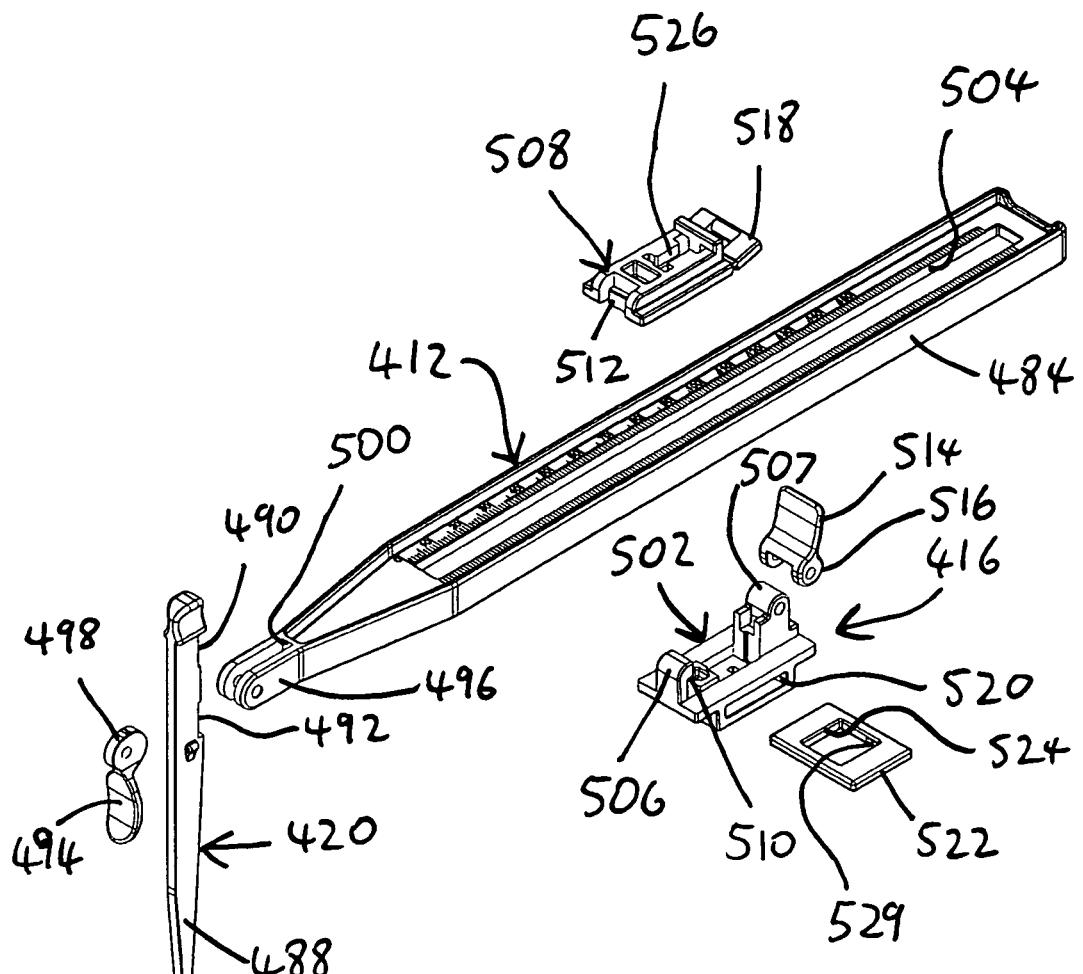
FIG. 24 is an exploded view of a surgical positioning device showing a securing assembly and a locating arrangement.

Reference is now made to FIG. 24, which shows the surgical positioning device 412 and the securing assembly 416. The surgical positioning device 412 comprises an elongate arm 484 having the adjustable indicating arrangement 420 mounted thereon. The indicating arrangement comprises a movable indicating member 488, which defines upper and lower notches 490, 492 to allow the position of the indicating member to be moved relative to the elongate arm 484 between first and second indicating positions.

A fastening lever 494 is pivotally mounted at the end region, constituting a fixed portion 496, of the elongate arm 484. The fastening lever 494 has a cam member 498 thereon which engages the Indicating member 488 when the fastening lever 494 is moved from a non-fastening position to a fastening position. In FIG. 23, the fastening lever 494 is in the fastening position, in which the cam member 498 pushes the Indicating member 488 against a wall 500, thereby clamping the indicating member against the wall 500.

The securing assembly 416 comprises a first holding member in the form of a lower holding member 502 mounted beneath the elongate arm 484. The elongate arm defines an elongate slot 504 extending along a major proportion of the length of the elongate arm 484. The lower portion 502 has front and rear projecting connection members 506, 507 which project through the slot 504 when the lower portion 502 is mounted on the elongate arm 484.

The securing assembly 416 also includes a second holding member, in the form of an upper holding member 508. The upper holding member 508 is mounted on top of the elongate arm 484. The front and rear connecting members 506, 507 include first detent formations 510 that cooperate with second formations 512 on the upper holding member 508 to secure the upper and lower holding members 502, 508 to each other and, thereby, to the elongate arm 484.

A securing lever 514 is pivotally mounted on the rear connecting member 507, and includes a cam member 516. A flap member 518 is pivotally mounted on the upper holding member 508. The cam member 516 engages the flap member 518 and, when the lever 514 is moved to a clamping position, the cam member 516 pushes the flap member 518 onto the elongate arm 484. This clamps the flap member 518 against the elongate arm 484, thereby securing the securing assembly 416, and hence the locating arrangement, in a desired position along the arm 484.

The lower holding member 502 defines a passage 520 for a locking slide 522. The locking slide defines a rectangular aperture 524, through which the locating post 432 extends. The upper and lower holding members 502, 508 also define H-shaped apertures 526, being of a corresponding shape to the cross-sectional profile of the locating post 432.

When the locking slide 522 is centrally arranged within the passage 520, the locating post can slide up and down within the apertures 526. However, when the locking slide 522 is pushed to a locking position at one side within the passage 520, it engages the locating post 432, thereby securing the locating post 432 in a desired position. The locating post 432 has a plurality of securing formations in the form of serrations 528 (see FIG. 25). The locking slide 522 has a projecting formation 529 which extends into the aperture 524. When the locking slide is moved to its locking position, the projecting formation 529 engages the serrations 528, thereby locking the locating post 432 in a desired position.

Figure 25:
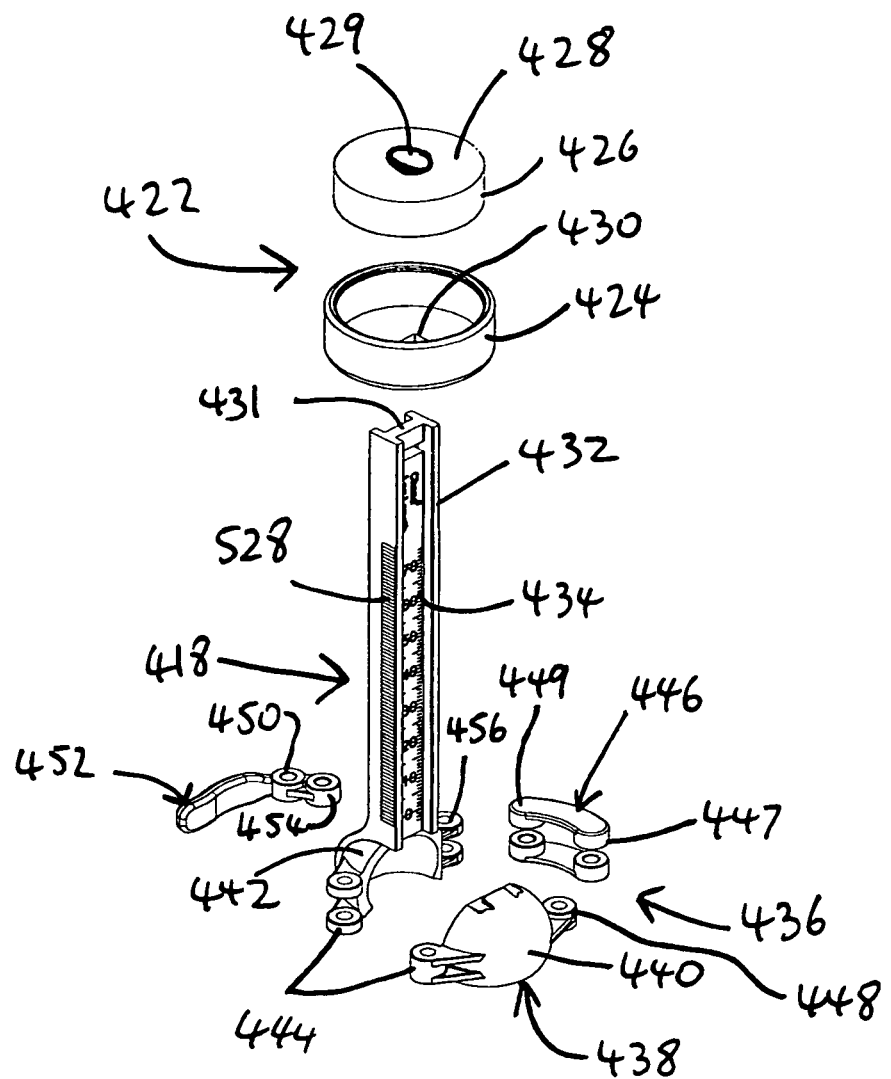
FIG. 25 is an exploded view of a locating arrangement.

FIG. 25 shows the locating arrangement 418, which comprises an elongate locating member in the form of a locating post 432, which is graduated by markings 434 in millimeters. The locating post 432 has an H-shaped cross-sectional profile, as shown.

A fastening assembly 436 is provided at the lower end of the locating post 432. The fastening assembly 436 comprises a clamping arrangement 438 comprising a first clamping member 440 pivotally attached to a second clamping member 442 at a main pivot 444. The second clamping member 442 is fixedly attached to the locating post 432. A fastening link 446 is pivotally attached at one end 447 thereof to a first pivot member 448 on the first clamping member 440 opposite the main pivot 444.

The opposite end 449 of the fastening link 446 is pivotally attached to a proximal pivot member 450 on a lever 452. The lever 452 also has a distal pivot member 454, adjacent the proximal pivot member 450. The distal pivot member 454 pivotally attaches the lever 452 to a second pivot member 456 on the second clamping member opposite the main pivot 444.

The lever 452 is pivotally movable between a clamping position (shown in FIG. 23), in which the first and second clamping members are pulled against one another, and a released position (not shown), in which the clamping members are moved apart from one another.

FIG. 25 also shows the components of the levelling device 422, which comprise a cylindrical holder 424 and a cylindrical liquid filled member in the form of a spirit level 426. The spirit level 426 comprise a transparent wall in the form of an upper cover 428 made of a transparent material such as glass or clear plastic. A marked region in the form of a circular marking 429 is provided on the cover 428 at a central region thereof. The spirit level 426 contains a liquid in which an air bubble is contained. When the spirit level 426 is upright, the air bubble is aligned with the circular marking 429. The levelling device 422 is attached to the locating post 432 by a dip 430 which clips onto an engaging bar 431 on the locating post 432.

Figure 26:
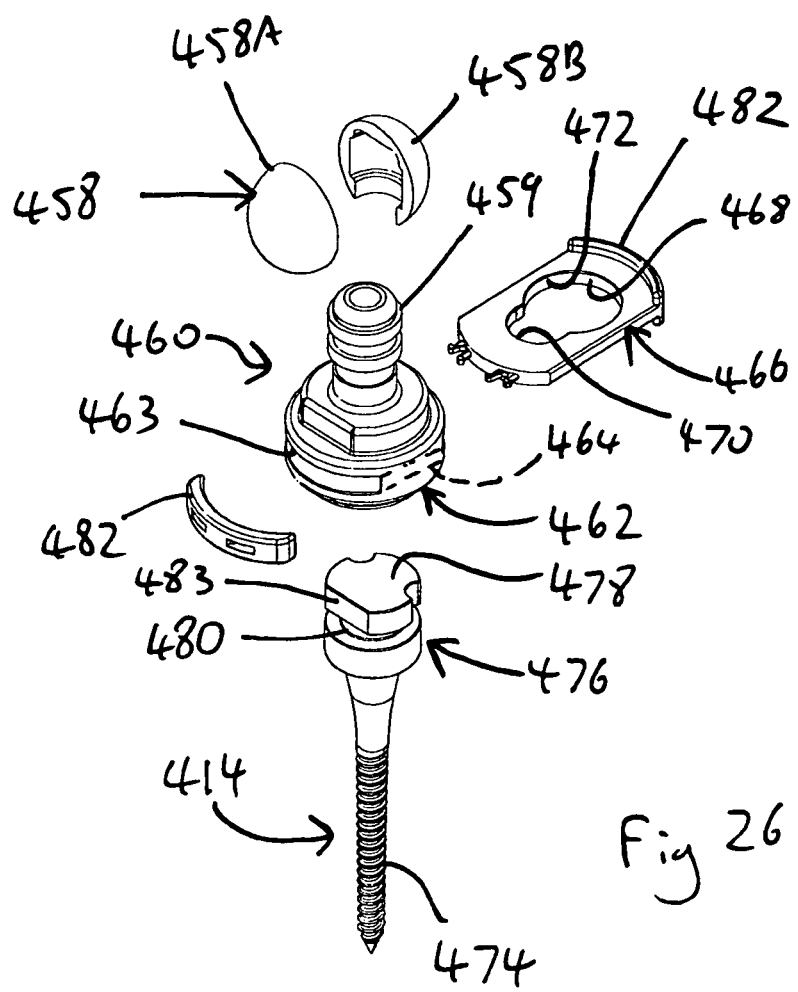
FIG. 26 is an exploded view of a fastening assembly and a marker element to be fastened by the fastening assembly.

Referring to FIG. 26, the fastening assembly 436 is used to clamp a clampable member, in the form of a ball member 458, which is provided on a location body 460. The ball member 458 is provided in two ball portions 458A and 458B, which are mounted around an upper mounting portion in the form of a spigot 459.

The location body 460 comprises a lower marker engaging portion 462 and the spigot 459 upon which the ball member 458 is mounted.

The marker engaging portion 462 defines opposed openings 463 and a pathway 464 communicating between the openings 463 through the marker engaging portion 462. The marker engaging portion 462 defines a recess (not shown) to receive the head 476. The pathway 464 extends through the recess. A locking member in the form of a locking plate 466 is received in the pathway 464 via the openings 463. The locking plate 466 defines an aperture 468 having a narrower section 470 and a wider section 472, and is slidable within the pathway 464 between locking and non-locking positions.

The screw 414 has a threaded shank 474 and a head 476 having a wider securing portion 478 and a narrower neck portion 480. The marker engaging portion 462 defines a recess to receive the head 476. When the locking plate 466 is in its locking position, the narrower section 470 of the aperture 468 is disposed around the neck portion 480. The narrower section 470 is narrower than the securing portion 478, thereby securing the screw 414 to the location body 460.

When the locking plate 466 is in its non-locking position, the larger section 472 of the aperture 468 is around the neck portion 480. The larger section 472 of the aperture 468 is wider than the securing portion 478, thereby allowing the securing portion to pass therethrough.

The locking plate 466 has front and rear flange members 482 preventing inadvertent removal of the locking plate from the pathway 464.

The securing portion 478 has a flat 483, and the recess in the marker engaging portion has a corresponding flat to ensure that the head 476 can be received in the marker engaging portion in only one orientation.

Figure 28:
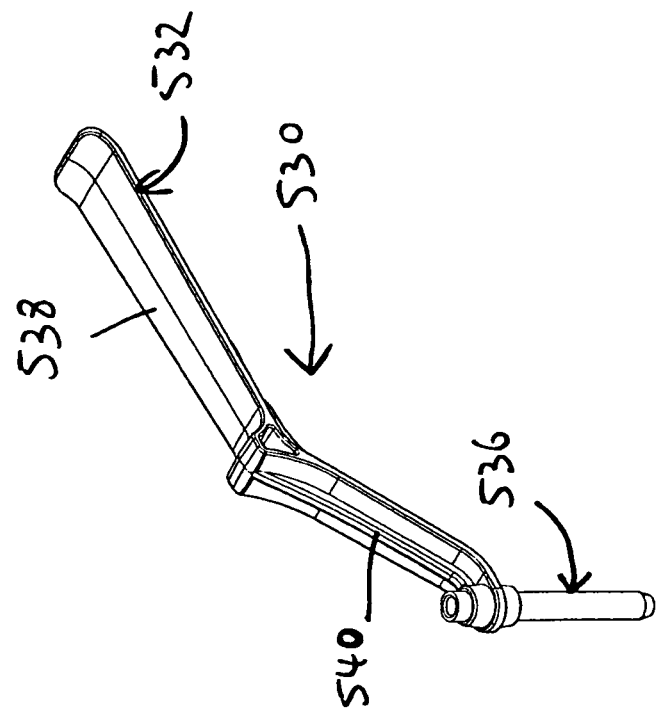
FIG. 28 shows the drill guide inserted into the drill guide handle.
Figure 27:
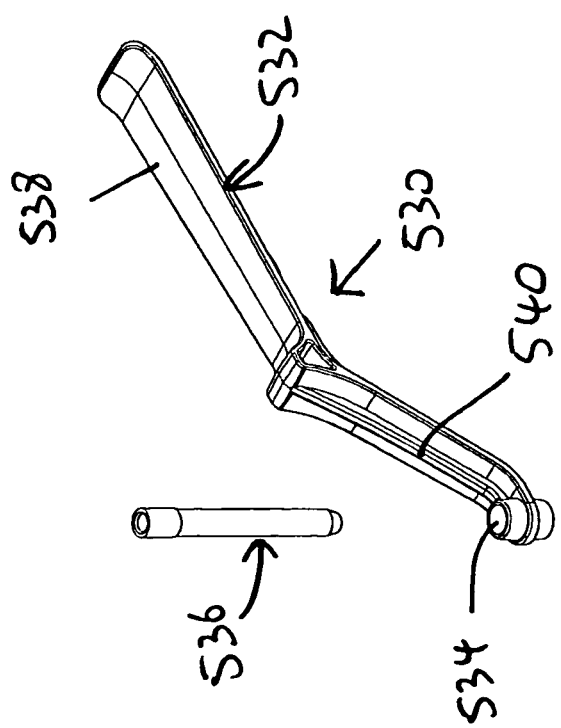
FIG. 27 shows a drill guide being inserted into a drill guide handle.

FIGS. 27 and 28 show a drill guide 530, which comprises a drill guide handle 532 defining an aperture 534 at one end. The drill guide 530 also includes a drill guide insert 536 for insertion into the aperture 534, to be held by the handle 532, as shown in FIG. 28.

Figure 30:
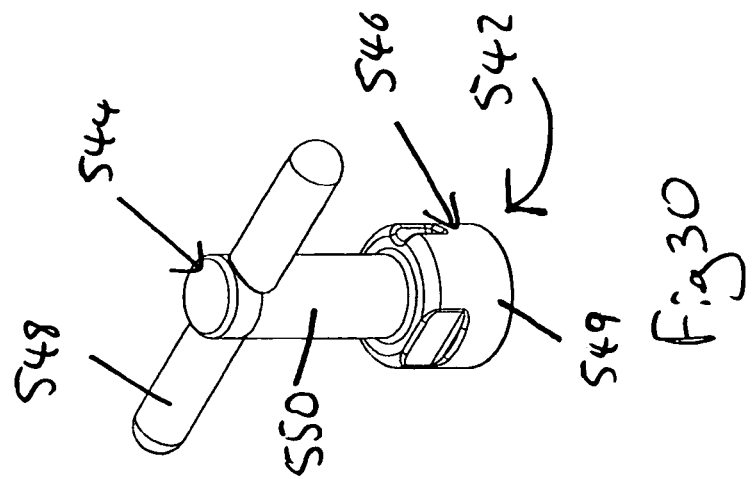
FIG. 30 is an assembled view of the tool shown in FIG. 27.
Figure 29:
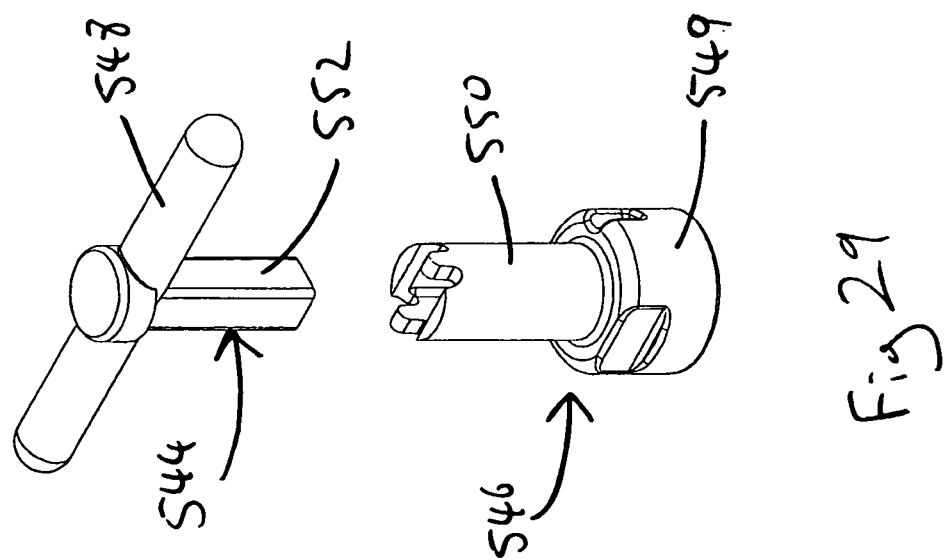
FIG. 29 is an exploded view of a tool for use with a marker element.

In use, the drill guide 530 is arranged at the appropriate place on the pelvis of the patient, and drill (not shown) is brought up to the drill guide insert 536 and pushed into the drill guide insert 536 to the pelvis to drill a hole therein. The datum screw 414 is then screwed into the hole in the pelvis using a tool 542, as shown in FIGS. 29 and 30.

The drill guide handle 532 has a holding portion 538 by which the handle 532 can be held, and a carrying portion 540 to carry the drill guide insert 536. The carrying portion 540 is angled relative to the holding portion 538 at a desired angle for ease of use.

The tool 542 comprises a T-bar 544 mounted on a screw engaging portion 546. The T-bar 544 has a cross member 548 to allow the tool 542 to be turned to screw in the datum screw 414. The screw engaging portion 546 has a socket portion 549, defining a socket (not shown) which is generally the same shape and size as the securing portion 478 of the head 476 of the screw 414, thereby allowing the screw to be turned by the tool 542.

The screw engaging portion 546 also has a T-bar locating portion 550 extending from the socket portion. The T-bar 544 has a spigot portion 552 which is received by the T-bar locating portion 550, to secure the T-bar on the screw engaging portion 546.

The invention claimed is:

1. A surgical positioning apparatus comprising:
   a surgical positioning device, the surgical positioning device comprising:
   a securing assembly,
   a locating arrangement securable to the securing assembly in a selected position of the locating arrangement,
   an indicating arrangement securable to the securing assembly in a selected position of the indicating arrangement,
   wherein the locating arrangement comprises a locating member to locate the positioning device in a desired orientation relative to a first article, and the indicating arrangement comprises an indicating member to indicate the position of a second article relative to the first article,
   wherein the apparatus further comprises a marker element configured to be mounted on the first article, the marker element comprising a co-operating formation to co-operate with the locating member and hold the locating member on the marker element,
   wherein the locating arrangement comprises an elongate member that has a fastening assembly provided thereon,
   wherein the fastening assembly comprises a clamping arrangement, which comprises a first clamping member and a second clamping member, wherein each clamping member is movable between clamping and released conditions, with the fastening assembly including a location means that the clamping arrangement is configured to clamp when the first and second clamping members are in the clamping position, said location means comprising a location body and a clampable member, with the location body being configured to mount the locating arrangement on the marker element;
   and
   a levelling device, wherein the levelling device is configured to be mounted on the surgical positioning device to facilitate orientation of the surgical positioning device relative to a selected position.

2. The surgical positioning apparatus according to claim 1, wherein the location body comprises a marker engaging portion and an upper mounting portion.

3. The surgical positioning apparatus according to claim 2, wherein the clampable member is provided on the upper mounting portion.

4. The surgical positioning apparatus according to claim 2, wherein the location means includes a locking member, and wherein the marker engaging portion defines a pathway therethrough into which the locking member is configured to be received.

5. The surgical positioning apparatus according to claim 4, wherein the locking member defines an aperture, which has a narrower section and a wider section, wherein the wider section is wider than the narrower section.

6. The surgical positioning apparatus according to claim 5, wherein the marker element has a head having a wider securing portion and a narrower neck portion, wherein the wider securing portion is wider than the narrower neck portion.

7. The surgical positioning apparatus according to claim 6, wherein when the locking member is in the non-locking position, the wider section of the locking member aperture is disposed around the neck portion.

8. The surgical positioning apparatus according to claim 4, wherein:

the locking member is in the form of a locking plate, with the locking plate defining an aperture having a narrower section and a wider section, wherein the wider section is wider than the narrower section, and wherein the locking plate is slidable within the pathway between locking and non-locking positions;

the marker element is a screw that has a threaded shank and a head having a wider securing portion and a narrower neck portion, wherein the wider securing portion is wider than the narrower neck portion;

the marker engaging portion defines a recess to receive the head of the screw; and wherein when the locking plate is in its locking position, the narrower section of the aperture is disposed around the neck portion, thereby securing the screw to the location body due to the narrower section being narrower than the securing portion, and wherein when the locking plate is in its non-locking position, the wider section of the aperture is around the neck portion, thereby allowing the securing portion to pass therethrough due to the wider section of the aperture being wider than the securing portion.

9. The surgical positioning apparatus according to claim 8, wherein the locking plate has front and rear flange members configured to prevent inadvertent removal of the locking plate from the pathway.

10. The surgical positioning apparatus according to claim 8, wherein the head of the screw is configured to be received in the marker engaging portion in only one orientation.

11. The surgical positioning apparatus according to claim 10, wherein the securing portion has a flat portion, and the recess in the marker engaging portion has a corresponding flat portion, to ensure that the head of the screw is configured to be received in the marker engaging portion in only one orientation.

12. The surgical positioning apparatus according to claim 1, wherein the elongate member has an H-shaped cross-sectional profile.

13. The surgical positioning apparatus according to claim 12, wherein the locating arrangement is slidably movable relative to the securing assembly.

14. The surgical positioning apparatus according to claim 13, wherein the first clamping member is pivotally attached to the second clamping member at a main pivot, and a fastening link is pivotally attached to the first clamping member.

15. The surgical positioning apparatus according to claim 14, comprising a clamping lever pivotally attached to the second clamping member, wherein the fastening link is pivotally attached to the lever, the lever being pivotally movable between a clamping position in which the first and second clamping members are pulled against one another, and a released position, in which the first and second clamping members are moved apart from one another.

16. The surgical positioning apparatus according to claim 15, wherein the clamping arrangement is configured to clamp the location means when the first and second clamping members are in the clamping position.

17. The surgical positioning apparatus according to claim 16, wherein the clampable member comprises a ball member, and the location body is configured to mount the locating arrangement on a marker element.

18. The surgical positioning apparatus according to claim 17, wherein the location body comprises a marker engaging portion for engaging the marker element, and also includes an upper mounting portion, the clampable member being provided on the upper mounting portion.

19. The surgical positioning apparatus according to claim 18, wherein the location means includes a locking member, and the marker engaging portion defines a pathway therethrough into which the locking member is configured to be received, the locking member defining an aperture, having a first section and second section, the first section being smaller than the second section, and wherein the locking member is slidable within the pathway between locking and non-locking positions, whereby when the locking member is in the locking position, a portion of the marker element is received in the smaller section, thereby locking the marker element to the fastening assembly.

20. The surgical positioning apparatus according to claim 19, wherein the marker element has a head having a wider securing portion and a narrower neck portion, whereby when the locking member is in the locking position, the neck portion is received in the first section of the aperture, thereby securing the marker element to the location body.

21. The surgical positioning apparatus according to claim 1, wherein the clampable member comprises a ball member.

22. The surgical positioning apparatus according to claim 1, wherein the indicating arrangement is movable linearly relative to the surgical positioning device.

23. The surgical positioning apparatus according to claim 1, wherein the marker element comprising a co-operating formation to co-operate with the locating member and hold the locating member on the marker element.

24. A surgical positioning apparatus comprising:
a surgical positioning device, the surgical positioning device comprising:
a securing assembly,
a locating arrangement securable to the securing assembly in a selected position of the locating arrangement,
an indicating arrangement securable to the securing assembly in a selected position of the indicating arrangement,
wherein the locating arrangement comprises a locating member to locate the positioning device in a desired orientation relative to a first article, and the indicating arrangement comprises an indicating member to indicate the position of a second article relative to the first article,
wherein the locating arrangement is slidably movable relative to the securing assembly and comprises an elongate member, having an H-shaped cross-sectional profile; and
a levelling device, wherein the levelling device is configured to be mounted on the surgical positioning device to facilitate orientation of the surgical positioning device relative to a selected position.

25. A surgical positioning apparatus comprising:
a surgical positioning device, the surgical positioning device comprising:
a securing assembly,
a locating arrangement securable to the securing assembly in a selected position of the locating arrangement,
an indicating arrangement securable to the securing assembly in a selected position of the indicating arrangement,
wherein the locating arrangement comprises a locating member to locate the positioning device in a desired orientation relative to a first article, and the indicating arrangement comprises an indicating member to indicate the position of a second article relative to the first article, wherein the locating arrangement is slidably movable relative to the securing assembly and comprises an elongate member, having an H-shaped cross-sectional profile, wherein a fastening assembly is provided on the elongate member, the fastening assembly comprising a clamping arrangement, having a first clamping member and a second clamping member, wherein the clamping members are movable between clamping and released conditions, the first clamping member being pivotally attached to the second clamping member at a main pivot, and a fastening link being pivotally attached to the first clamping member; and a levelling device, wherein the levelling device is configured to be mounted on the surgical positioning device to facilitate orientation of the surgical positioning device relative to a selected position.

* * * * *